(12) United States Patent
Shigeno et al.

(10) Patent No.: US 9,961,985 B2
(45) Date of Patent: May 8, 2018

(54) CASE FOR POWERED TOOTHBRUSH AND SYSTEM

(71) Applicants: COLGATE-PALMOLIVE COMPANY, New York, NY (US); Omron Healthcare Co., Ltd., Kyoto (JP)

(72) Inventors: Takashi Shigeno, Tokyo (JP); Kazuya Andachi, Tokyo (JP); Tamaki Ito, Kyoto (JP)

(73) Assignee: Colgate-Palmolive Company, New York, NY (US)

( * ) Notice: Subject to any disclaimer, the term of this patent is extended or adjusted under 35 U.S.C. 154(b) by 548 days.

(21) Appl. No.: 14/090,884

(22) Filed: Nov. 26, 2013

(65) Prior Publication Data
US 2014/0150189 A1 Jun. 5, 2014

Related U.S. Application Data

(63) Continuation-in-part of application No. 29/456,353, filed on May 30, 2013, now Pat. No. Des. 757,439.
(Continued)

(30) Foreign Application Priority Data

Nov. 30, 2012 (JP) .................. 2012-029430
Nov. 30, 2012 (JP) .................. 2012-029431
Nov. 30, 2012 (JP) .................. 2012-029432

(51) Int. Cl.
*H02J 7/00* (2006.01)
*A45D 44/18* (2006.01)
(Continued)

(52) U.S. Cl.
CPC ............ *A45D 44/18* (2013.01); *A61C 17/224* (2013.01); *A61C 19/02* (2013.01)

(58) Field of Classification Search
USPC ......................................................... 320/108
See application file for complete search history.

(56) References Cited

U.S. PATENT DOCUMENTS 677,785 A 7/1901 Mariner
1,008,523 A 11/1911 Boyle
(Continued)

FOREIGN PATENT DOCUMENTS

CN 201453403 5/2010
CN 201676306 12/2010
(Continued)

OTHER PUBLICATIONS

Bling Dental Products, "BlasterPRO Travel Charger & UV Sanitizer," located at www.blingdentalproducts.com/products/toothbrush-travel-charger-cases/blasterpro.html, accessed on Nov. 18, 2013.
(Continued)

*Primary Examiner* — Eric Lee

(57) ABSTRACT

A case for a powered toothbrush comprises a housing having an interior for receiving a powered toothbrush, and a cover, wherein the cover substantially obfuscates the interior but is sufficiently light-transmissive to communicate the presence of an indicator from within the interior. Also provided is a powered toothbrush and case system.

6 Claims, 12 Drawing Sheets

Related U.S. Application Data and a continuation-in-part of application No. 29/456,355, filed on May 30, 2013, now Pat. No. Des. 736,701, and a continuation-in-part of application No. 29/456,360, filed on May 30, 2013, now Pat. No. Des. 723,912.

(51) Int. Cl.
*A61C 17/22* (2006.01)
*A61C 19/02* (2006.01)

(56) References Cited

U.S. PATENT DOCUMENTS

| | | | |
|---|---|---|---|
| 3,194,621 A | 7/1965 | Frost | |
| 3,287,076 A | 11/1966 | Spofford | |
| 3,463,994 A | 8/1969 | Spohr | |
| 5,796,325 A * | 8/1998 | Lundell | A61C 17/22 336/233 |
| 6,027,081 A | 2/2000 | Rosenger | |
| 6,726,004 B2 | 4/2004 | Watson | |
| 6,753,537 B2 | 6/2004 | Woo | |
| D493,136 S | 7/2004 | Since | |
| 6,906,495 B2 | 6/2005 | Cheng et al. | |
| 6,910,717 B1 | 6/2005 | Moyer | |
| 7,320,397 B2 | 1/2008 | Chao | |
| 7,348,572 B2 * | 3/2008 | Shin | A61L 2/10 250/455.11 |
| 7,378,067 B2 | 5/2008 | Song et al. | |
| D622,406 S | 8/2010 | Russell, II et al. | |
| 8,373,387 B2 | 2/2013 | Bourilkov et al. | |
| 8,408,483 B2 | 4/2013 | Boyd et al. | |
| D683,731 S | 6/2013 | Chiu et al. | |
| 8,522,973 B2 | 9/2013 | McClenon Joseph | |
| 2006/0022636 A1 | 2/2006 | Xian et al. | |
| 2006/0027246 A1 | 2/2006 | Wilkinson | |
| 2007/0182367 A1 | 8/2007 | Partovi | |
| 2007/0279002 A1 * | 12/2007 | Partovi | H02J 7/0027 320/115 |
| 2008/0209650 A1 * | 9/2008 | Brewer | A46B 15/0002 15/22.1 |
| 2009/0127214 A1 | 5/2009 | Kruger et al. | |
| 2011/0100865 A1 * | 5/2011 | Brink | A61C 19/02 206/581 |
| 2011/0315572 A1 | 12/2011 | Vu et al. | |
| 2012/0192367 A1 | 8/2012 | Lin | |
| 2013/0277271 A1 | 10/2013 | Toulotte | |

FOREIGN PATENT DOCUMENTS

| | | |
|---|---|---|
| CN | 202069891 U | 12/2011 |
| CN | 202333855 | 7/2012 |
| CN | 202446285 | 9/2012 |
| CN | 102813558 | 12/2012 |
| CN | 202651859 U | 1/2013 |
| DE | 2646457 A1 | 4/1977 |
| GB | 1195209 A | 6/1970 |
| JP | H07263032 A | 10/1995 |
| JP | H0880220 A | 3/1996 |
| TW | M421808 | 2/2012 |
| WO | WO 2000/070999 A1 | 11/2000 |
| WO | WO 2000/74591 | 12/2000 |
| WO | WO 2003/096361 | 11/2003 |
| WO | WO 2003/096512 | 11/2003 |
| WO | WO 2004/038888 | 5/2004 |
| WO | WO 2005/037331 A1 | 4/2005 |
| WO | WO 2008/147360 | 12/2008 |
| WO | WO 2010/067328 | 6/2010 |

OTHER PUBLICATIONS

Group Buyer, "USB Rechargable Electric Toothbrush," published on Jul. 20, 2013, located at www.groupbuyer.com.hk/en/deal/osbert_paris_company_20130710, accessed on Nov. 22, 2013.

JaewanWorks, "In & Out," published in 2012, located at www.jaewanworks.com/in&out.html, accessed on Nov. 22, 2013.

Omron, "Toothbrush Electric HT-B601 Sound Wave PORTABLE White Japan NEW," released Feb. 15, 2013, located at www.ebay.com/itm/OMRON-Toothbrush-Electric-HT-B601-Sound-Wave-PORTABLE-White-Japan-NEW-/321250251956?pt=LH_DefaultDomain_0&hash=item4acc01d4b4, accessed on Nov. 18, 2013.

Philips, "sonicare DiamondClean," located at www.sonicare.com/professional/en_us/OurProducts/DiamondClean.aspx, accessed on Nov. 16, 2013.

Pursonic, "S1 Portable UV Toothbrush Sanitizer," located at www.pursonicusa.com/S1-Portable-UV-Toothbrush-Sanitizer/p-5, accessed on Nov. 22, 2013.

* cited by examiner

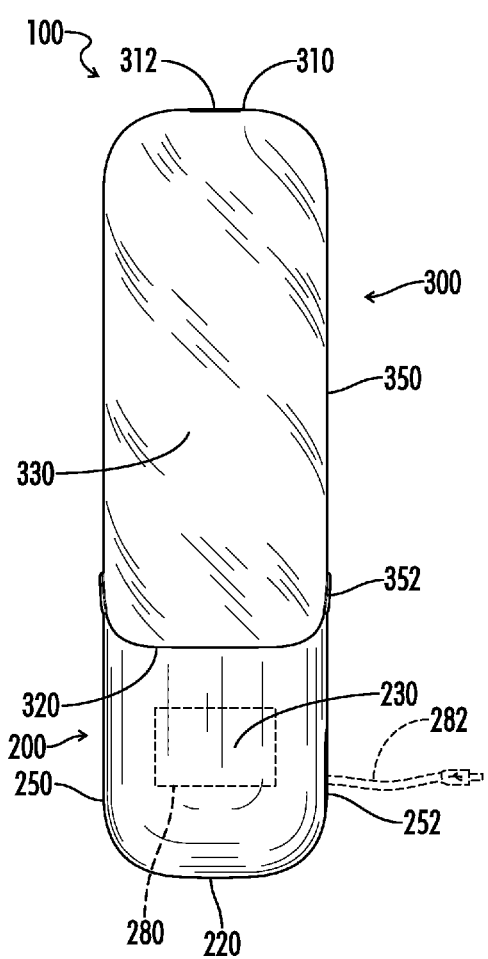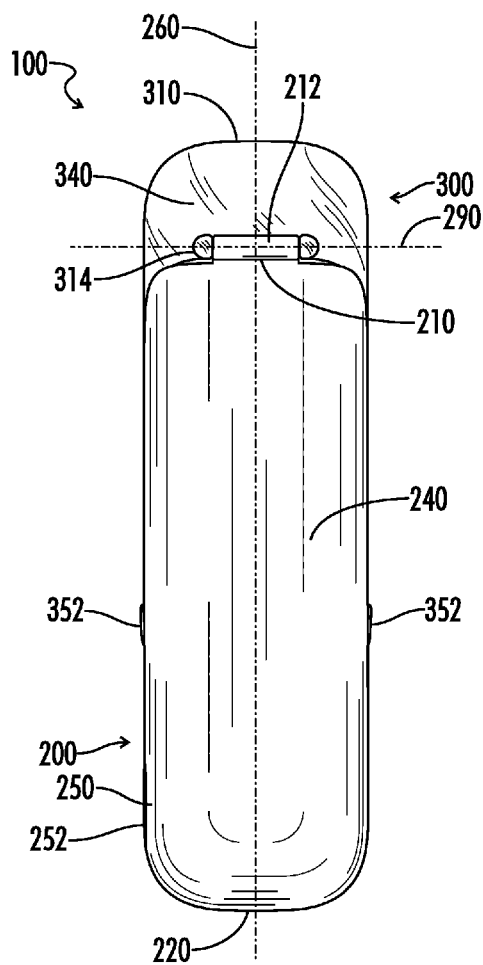

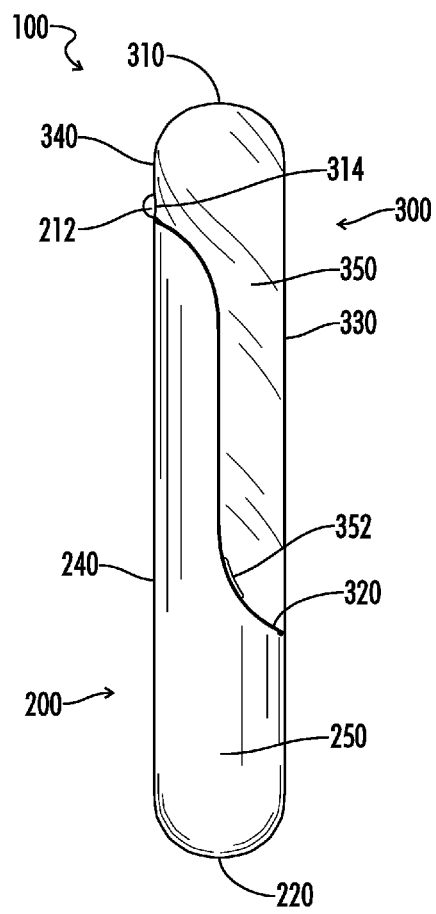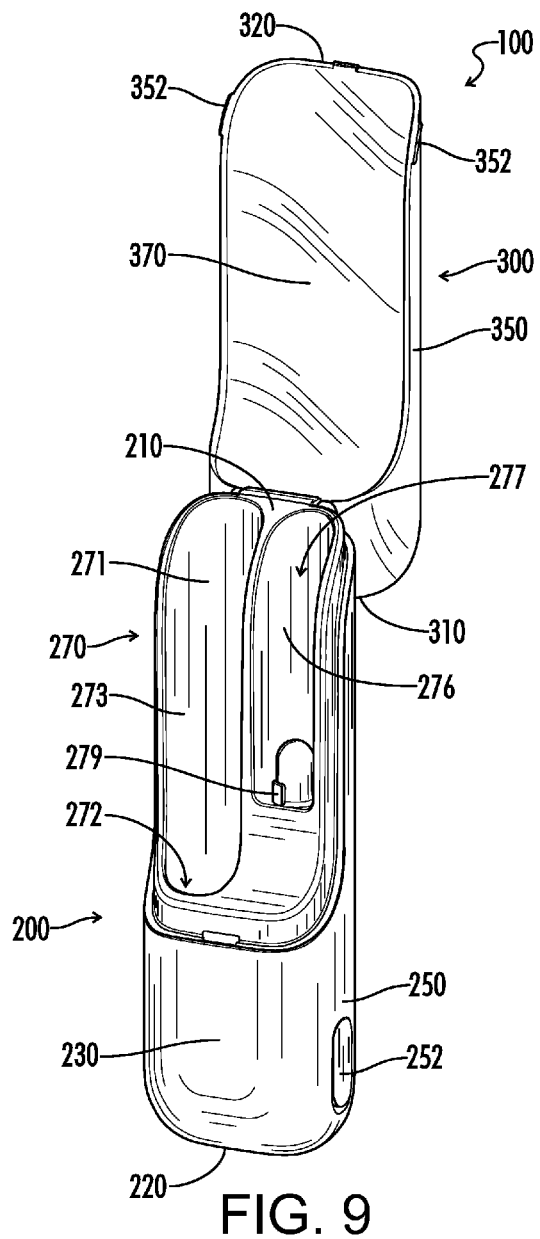

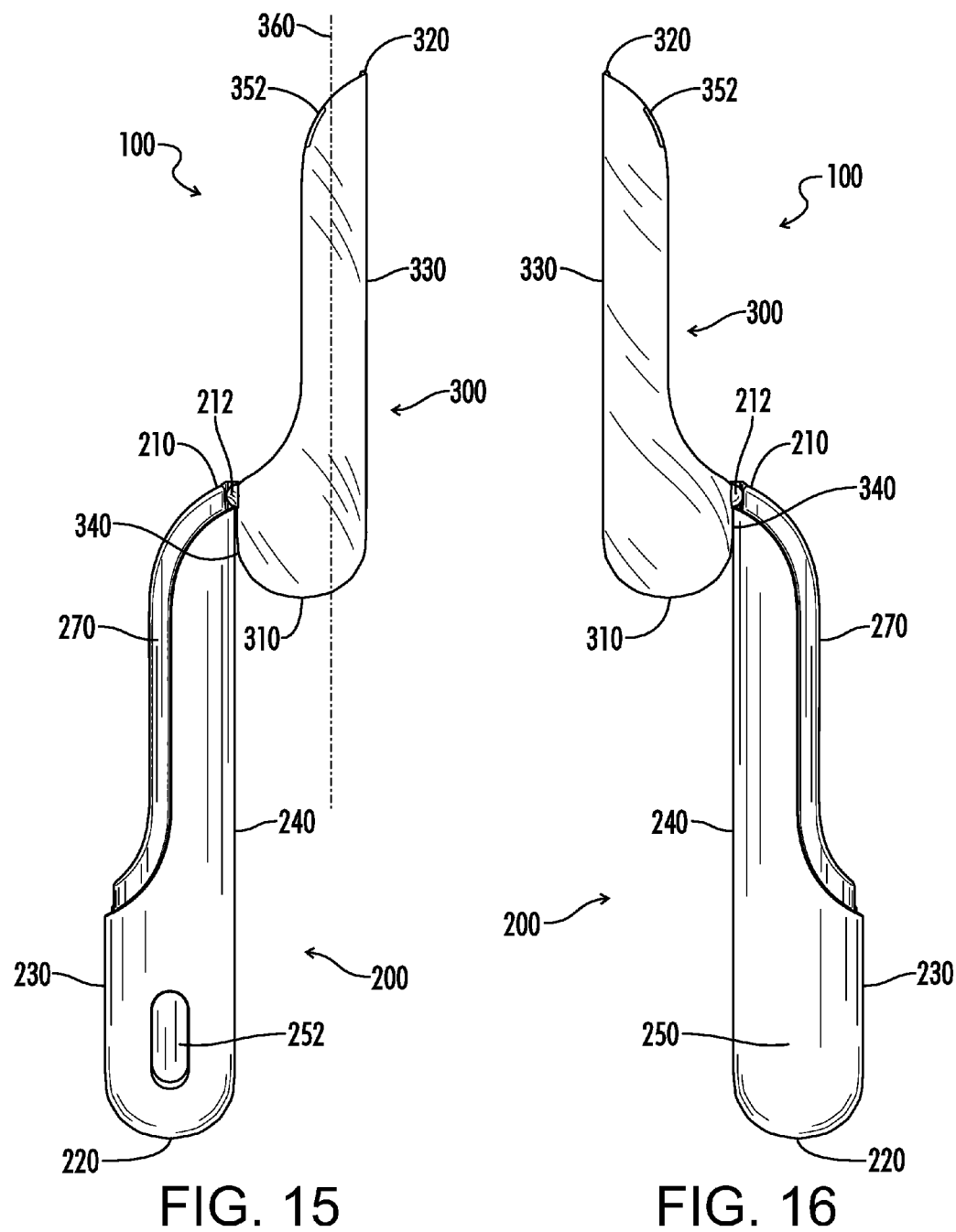

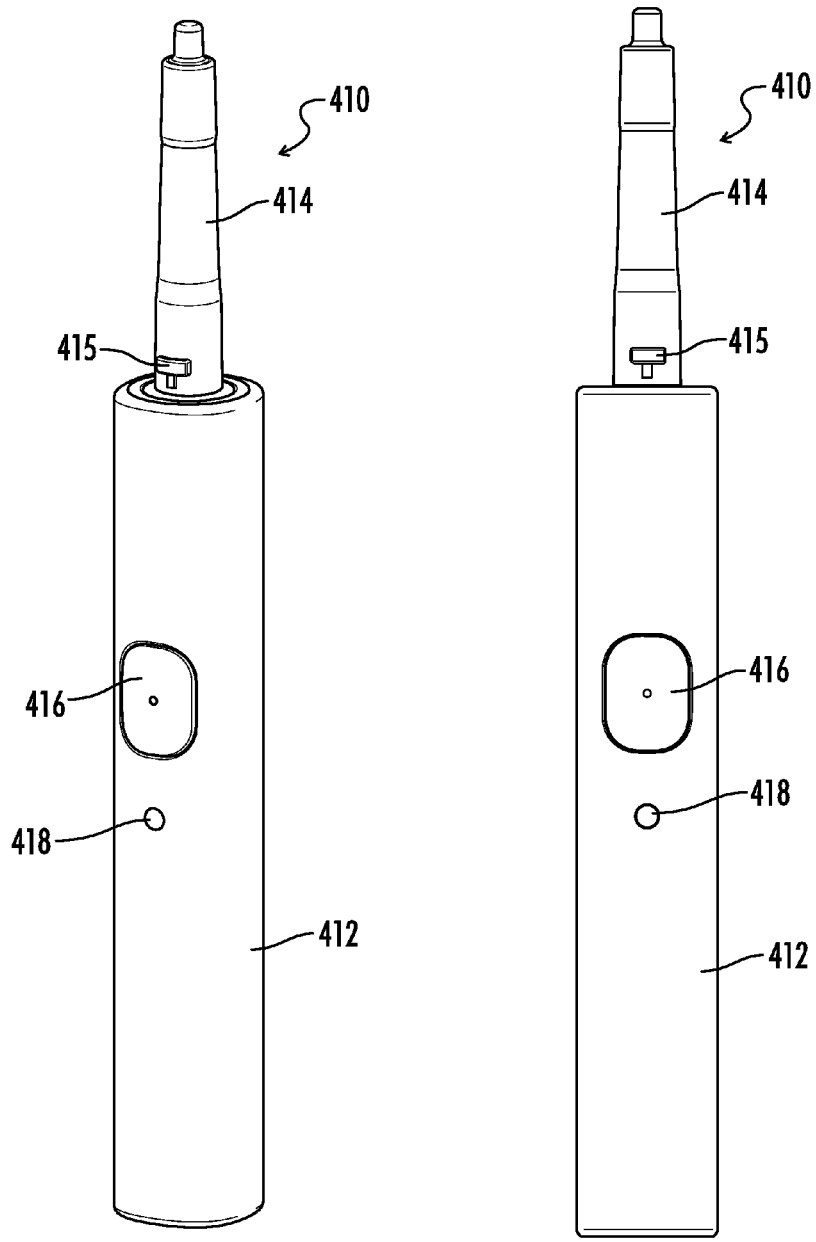

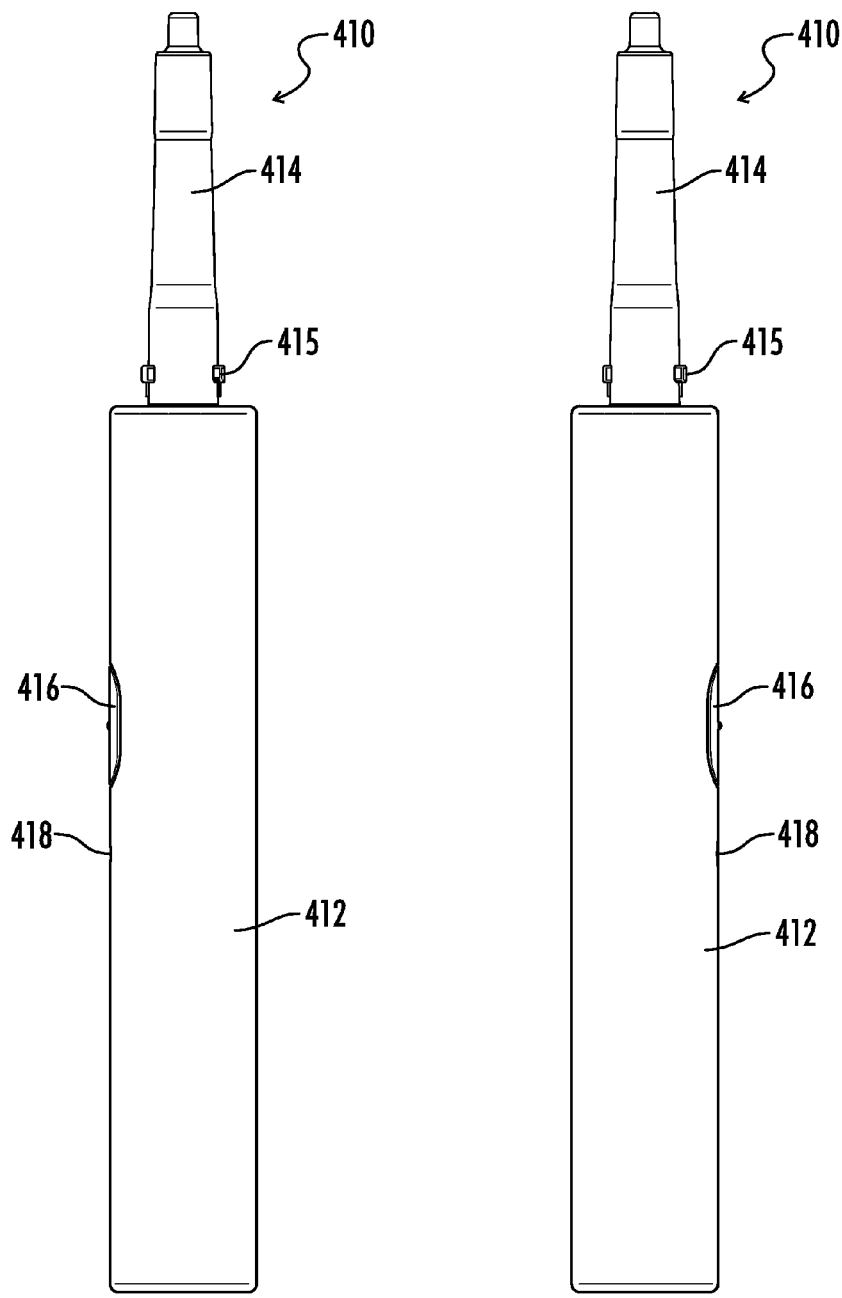

CASE FOR POWERED TOOTHBRUSH AND SYSTEM

CROSS-REFERENCE TO RELATED APPLICATIONS

This application is a continuation-in-part of (1) U.S. patent application Ser. No. 29/456,353 filed on May 30, 2013, which claims priority to Japan Patent Application No. 2012-029430 filed on Nov. 30, 2012, and (2) U.S. patent application Ser. No. 29/456,355 filed on May 30, 2013, which claims priority to Japan Patent Application No. 2012-029431 filed on Nov. 30, 2012, and (3) U.S. patent application Ser. No. 29/456,360 filed on May 30, 2013, which claims priority to Japan Patent Application No. 2012-029432 filed on Nov. 30, 2012. The disclosures of each of the above applications are incorporated herein by reference.

BACKGROUND

Other than travel toothbrushes having a bristle portion that is stored within a respective handle portion, typically by folding or collapsing the bristle portion into the handle portion, attention is rarely given to the manner in which travel toothbrushes are stored or contained. In some cases, a travel toothbrush is simply tossed in an unprotected state into a bag of mixed toiletries. In other cases, the toothbrush is stored within a container that is functionally unremarkable other than to provide air holes or other venting for the evaporation of residual moisture on the brush.

Additional storage considerations are required for travel toothbrushes that are powered. If the toothbrush is powered by batteries, then it may be necessary to store extra batteries, or a battery charger, or both. This may also necessitate the use or carrying of a power charging cord, and in some cases a power adapter or converter if traveling abroad. The number and complexity of peripherals may vary depending on the type of brush, duration of travel, the power supply structure of the various destinations, types and number of brush heads, and the like.

It can be somewhat challenging to remember and carry the various required peripherals during one's travels. However, it can be very aggravating if the manner in which the toothbrush is stored causes an inadvertent power drain as a result of the toothbrush being turned on when not in use. This can happen if the toothbrush is stored with a mix of other toiletries that inadvertently impacts the power switch on the toothbrush. This can also happen if the toothbrush is stored in a separate case that is relatively soft and susceptible to impact. Even with a sturdy storage container, the walls of the container may be opaque or may otherwise hide an inadvertent powered condition of a stored toothbrush that would only be manifest when it is time to brush and the user is left with no power.

Similar issues can arise with rechargeable powered toothbrushes that are charged through a storage case. The toothbrush or case is typically provided with an indicator light that signals a charging condition or a charging status of the toothbrush. The indicator light not only verifies that the toothbrush is being charged, but it also confirms the viability of the charging origin, such as whether the power outlet or power port is live and functioning properly. If a rechargeable toothbrush is placed within a case in order to charge the brush, and either the case hides the charging status of the toothbrush, and/or the charging outlet is not functioning properly, the owner of the brush would never know that the toothbrush is not being charged while the case is closed. This can be especially aggravating if the owner believes that the toothbrush was being charged when in fact the toothbrush was not.

It would be desirable, therefore, to have a travel toothbrush that is stored within a case that addresses some of the previously mentioned challenges and shortcomings. It would also be desirable to provide a storage case that communicates the power or charging condition of the toothbrush through the storage case without having to open the case.

BRIEF SUMMARY

A case for a powered toothbrush comprises a housing having an interior for receiving a powered toothbrush, and a cover, wherein the cover substantially obfuscates the interior but is sufficiently light-transmissive to communicate the presence of an indicator from within the interior. Also provided is a powered toothbrush and case system.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 3 is a front view thereof;

FIG. 4 is a rear view thereof;

FIG. 8 is a left side view thereof;

FIG. 9 is a perspective front view thereof, shown in an open configuration;

FIG. 15 is a right side view thereof;

FIG. 16 is a left side view thereof;

FIG. 17 is a perspective view of one embodiment of a portion of a powered toothbrush in accordance with the present disclosure;

FIG. 18 is a front view thereof;

FIG. 22 is a right side view thereof;

FIG. 23 is a left side view thereof;

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Figure 1:
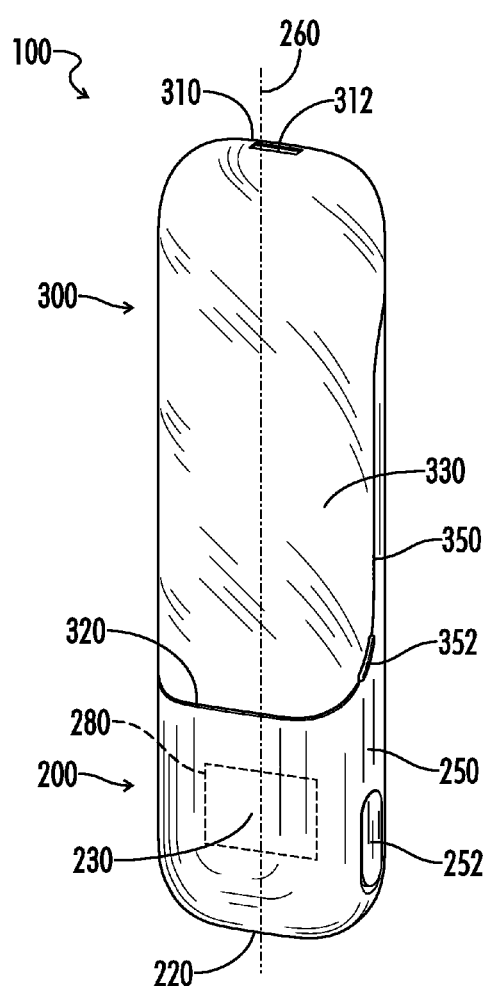
FIG. 1 is a perspective front view of one embodiment of a case in accordance with the present disclosure, shown in a closed configuration.
Figure 2:
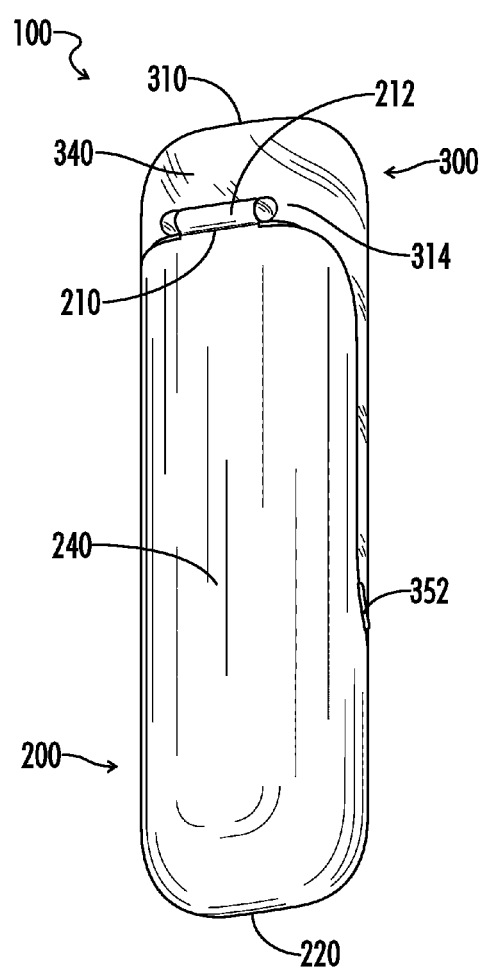
FIG. 2 is a perspective rear view thereof, shown in the closed configuration.
Figure 5:
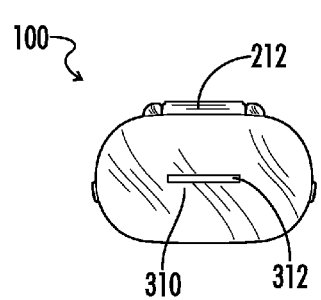
FIG. 5 is a top view thereof.
Figure 6:
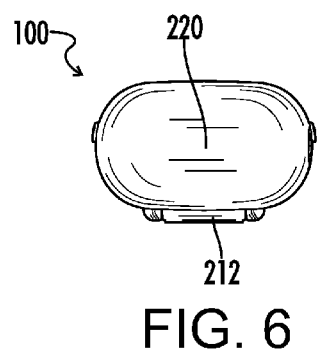
FIG. 6 is a bottom view thereof.
Figure 7:
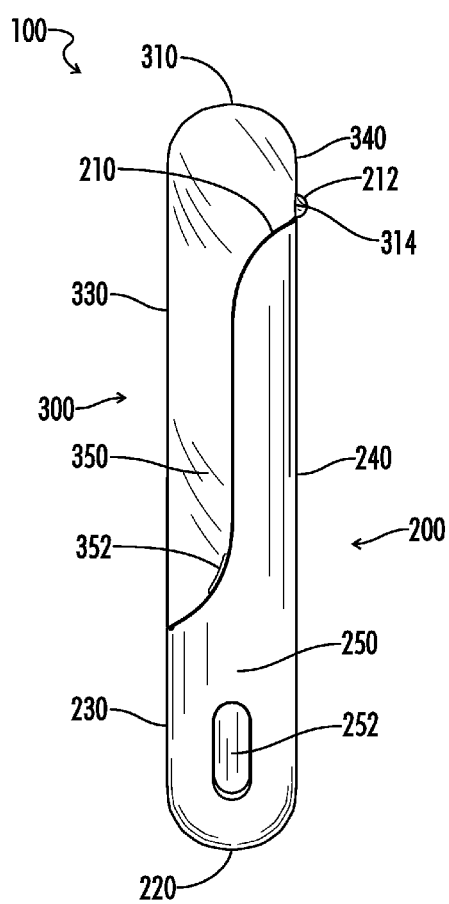
FIG. 7 is a right side view thereof.
Figure 10:
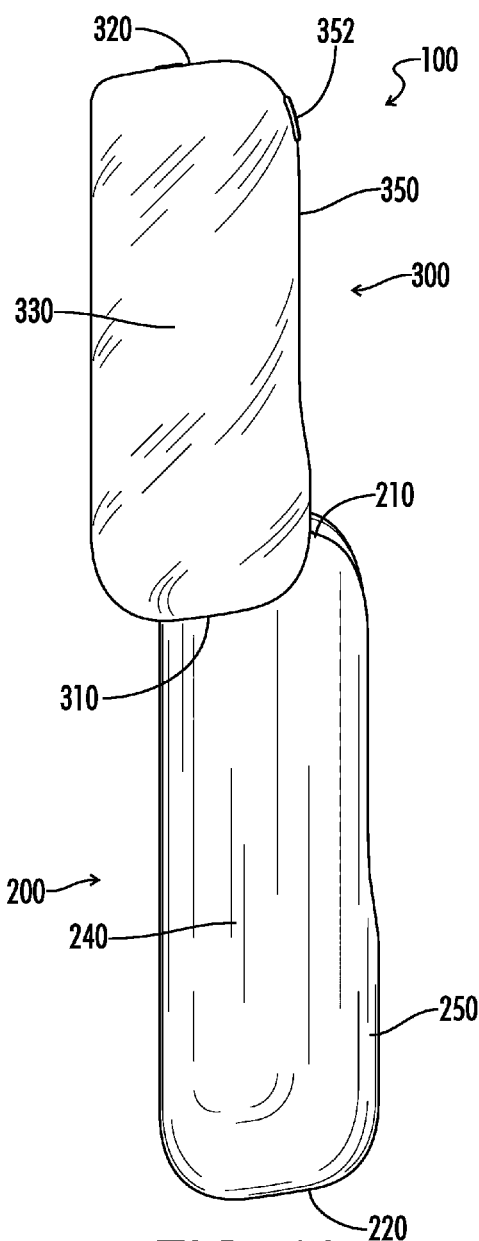
FIG. 10 is a perspective rear view thereof, shown in the open configuration.
Figure 11:
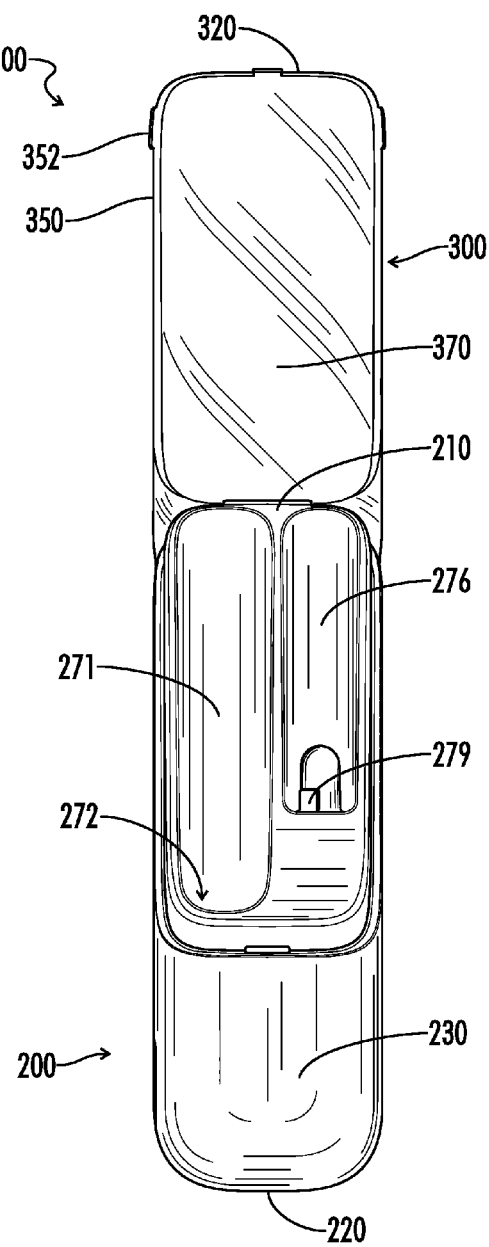
FIG. 11 is a front view thereof.
Figure 12:
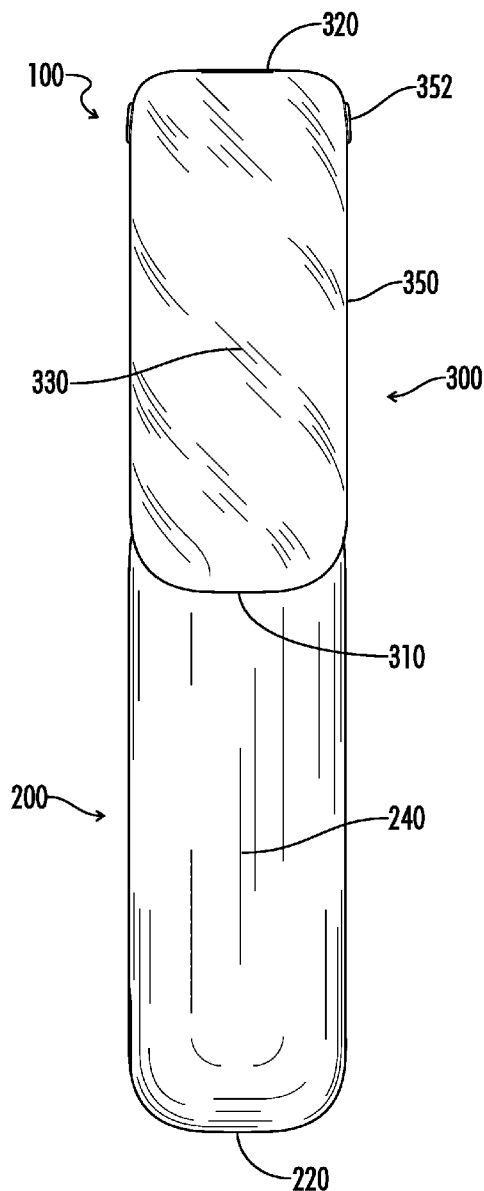
FIG. 12 is a rear view thereof.
Figure 13:
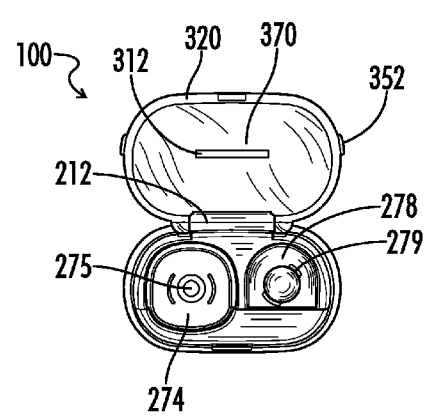
FIG. 13 is a top view thereof.
Figure 14:
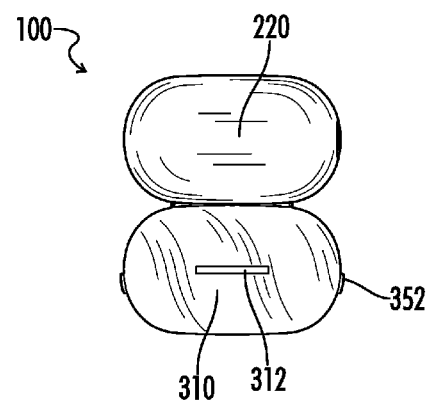
FIG. 14 is a bottom view thereof.
Figure 19:
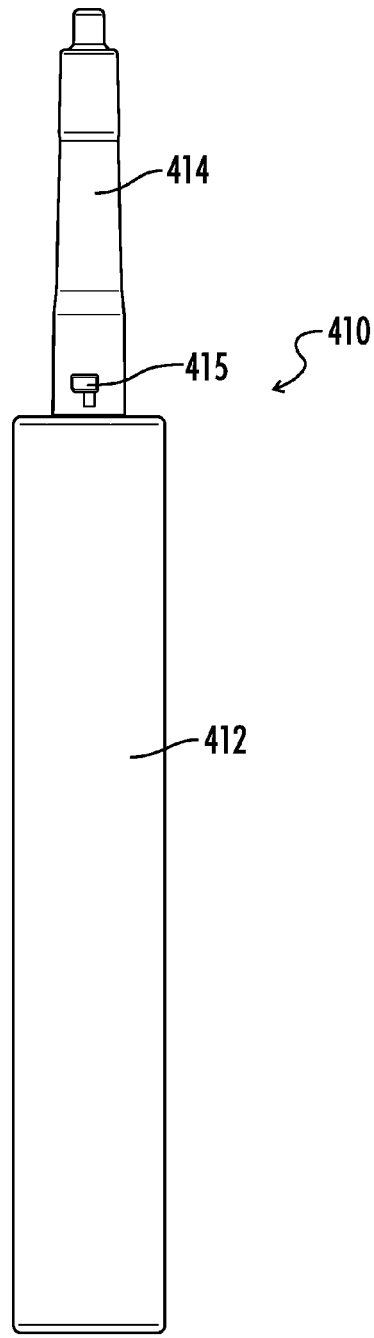
FIG. 19 is a rear view thereof.
Figure 20:
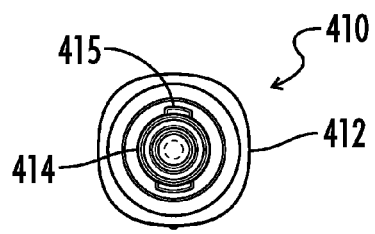
FIG. 20 is a top view thereof.
Figure 21:
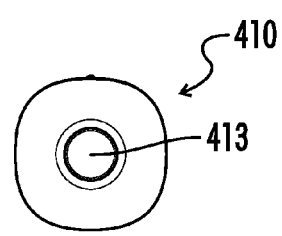
FIG. 21 is a bottom view thereof.
Figure 24:
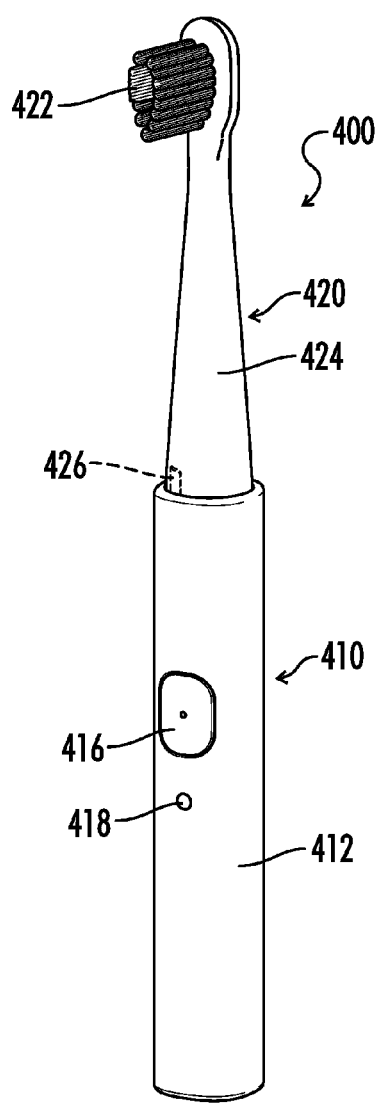
FIG. 24 is a perspective view of one embodiment of an assembled powered toothbrush in accordance with the present disclosure.
Figure 25:
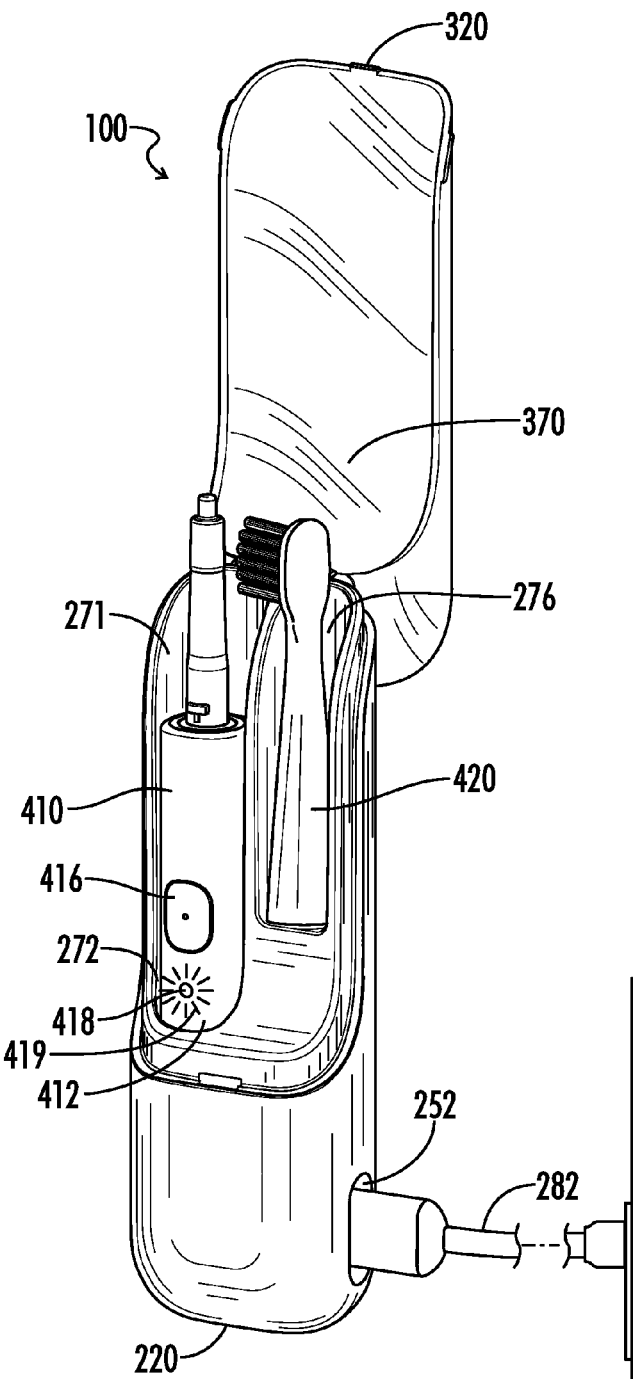
FIG. 25 is a perspective view of one embodiment of a powered toothbrush and case system including a disassembled powered toothbrush stored within one embodiment of an open case being charged in accordance with the present disclosure.
Figure 26:
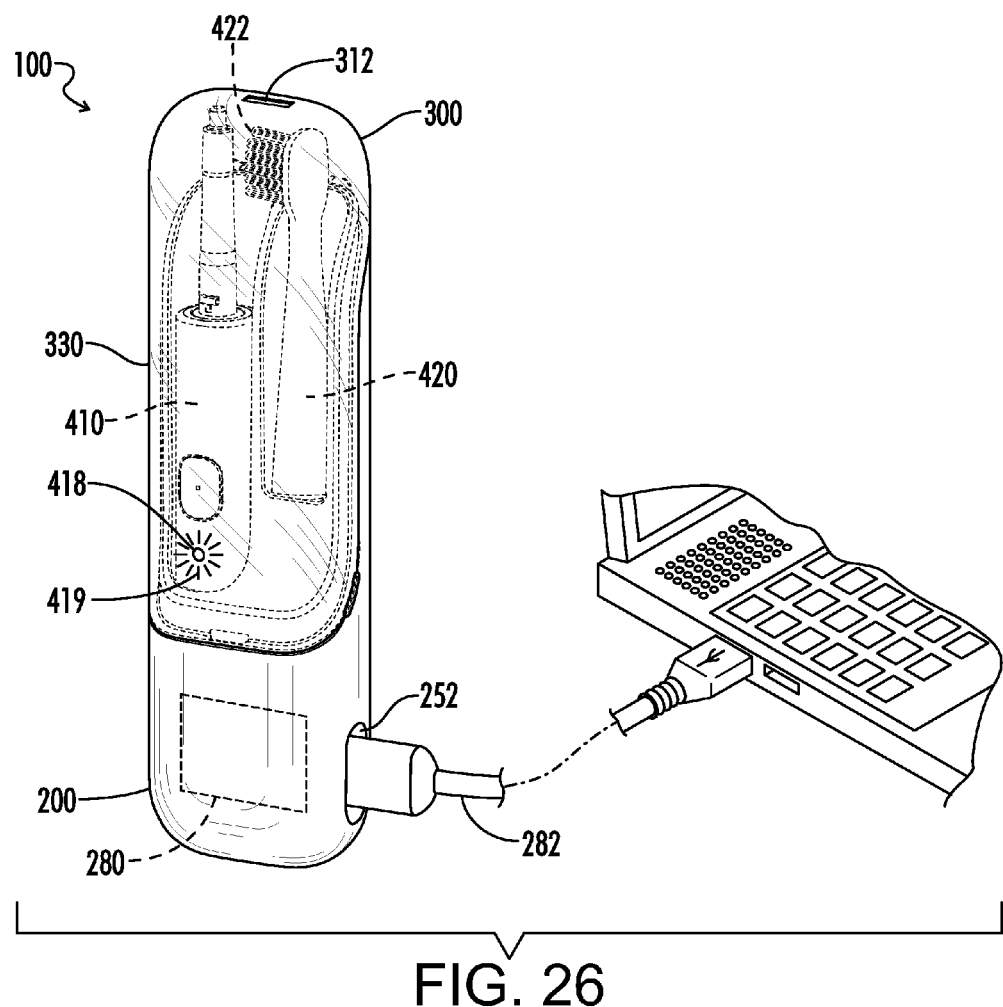
FIG. 26 is a perspective front view of one embodiment of a powered toothbrush and case system including a disassembled powered toothbrush stored within one embodiment of a closed case being charged in accordance with the present disclosure.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "front," "rear," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto FIGS. 1-16 illustrate one embodiment of a charging case 100 having a housing 200 and a cover 300 for receiving and storing a power toothbrush 400 (FIG. 24). The powered toothbrush 400 generally comprises a handle 410 and brush head 420, one embodiment of which is shown with reference to FIGS. 17-26, the details of which will be described later. FIGS. 25 and 26 illustrate embodiments of a powered toothbrush and case system including toothbrush components 410, 420 stored within case 100, with toothbrush component 410 being charged while the case 100 is connected to a power source. In the illustrated embodiments, the power source can be a power outlet (FIG. 25), computer (FIG. 26) or the like, with other power sources being possible. The charging of the toothbrush component 410 while seated within the case 100 is apparent through the illumination 419 of an indicator 418 on the toothbrush component 410, which illumination 419 is evident while the cover 300 is open (FIG. 25) or closed (FIG. 26). In the illustrated embodiment, once the toothbrush component 410 is charged, the components 410, 420 are removed from the case 100 and assembled (FIG. 24) prior to use. After use, the components 410, 420 are disassembled and stored within the case 100, and then if desired the case 100 is connected to a power source for charging the component 410. The powered aspect of the powered toothbrush can come in any form or type of benefit delivery, where the powered toothbrush may, for example, vibrate when activated, or deliver a therapeutic active, or emit beneficial or sanitizing light, or other types of benefits, with the present disclosure not being limited to any type of powered delivery or benefit, or any type of head, bristle, neck or stem configuration. Details of each component and aspects of the case and toothbrush system will now be described.

As shown in FIGS. 1-16, the case housing 200 further comprises a top end 210, a bottom end 220, a front surface 230, a rear surface 240, a side surface 250 having a charging port 252, a longitudinal axis 260 (FIG. 1), and an interior 270. A charger system 280 is provided for charging a power toothbrush 400 that is stored in the case 100 when a power source is connected to the housing 200 through the port 252 by a power cord 282 or the like (see FIGS. 3 and 25-26 for example). Additional details of the interaction between the power toothbrush 400 and the case 100 will be described below. In one embodiment, the port 252 can include a mini-USB connection, although connectors of other sizes and types are possible, and the charger 280 is an induction charger, although other types of chargers are also possible. The charger system 280 can also comprise an internal power source, such as a battery (not shown), that would render unnecessary the need to connect the case 100 to an external power source. Alternatively, the case 100 may include a charging system that can operate with one or both of an internal or external power source. Other charging variations are possible. Furthermore, the port 252 may be positioned in a location relative to the housing 200 other than as shown in the accompanying drawings, and may have an optional protective and/or waterproof cover as shown.

The cover 300 further comprises a top end 310 with a vent 312, a bottom end 320, a front surface 330, a rear surface 340, a side surface 350 with gripping tabs 352 for manipulating the cover 300 relative to the housing 200, a longitudinal axis 360 (FIG. 15), and an interior surface 370 (FIG. 9). While the vent 312 and gripping tabs 352 are preferably positioned relative to certain features of the cover 300, it will be appreciated that the vent 312 and/or gripping tabs 352 could be located elsewhere on the cover 300, or could be optional if desired.

In the illustrated embodiment, the housing interior 270 further comprises at least a first storage location 271 for receiving a first component 410 (FIGS. 17-26) of a powered toothbrush 400, the first storage location 271 having a storage chamber 272 at least partially surrounded by chamber walls 273 for receiving a portion of the first component 410, and a floor 274 (FIG. 13) upon which the first component 410 is seated while being stored and potentially charged. The housing interior 270 further comprises a second storage location 276 for receiving a second component 420 (FIGS. 24-26) of a powered toothbrush 400, the second storage location 276 having a storage chamber 277 for receiving a portion of the second component 420, and a floor 278 (FIG. 13) having a mounting pin with indexing tabs 279 thereon upon which the second component 420 can be mounted for storage. In the illustrated embodiment, the first and second components 410, 420 of the powered toothbrush 400 are stored separately within the storage locations 271, 276 respectively (FIGS. 25-26), and are then combined or attached to each other (FIG. 24) prior to use. In certain situations it may be preferable to store a powered toothbrush in a case as a single unit (not shown), in which case there would only be provided a single storage location (not shown). Other configurations are possible.

In the illustrated embodiment, the first component 410 of the powered toothbrush 400 further comprises a handle 412 having a slot 413 (FIG. 21), a stem 414 with indexing tabs 415 for receiving the second component 420 or brush head 420 in the illustrated embodiment, a power switch or button 416, and an indicator 418 that preferably illuminates 419 (FIGS. 25-26) when the powered toothbrush 400 is being charged while stored within the case 100. More specifically, the handle 412 is preferably slidably received within the storage chamber 272 with a portion of the storage chamber walls 273 partially enclosing the handle 412 to prevent the handle 412 from falling out of the chamber 272 unless the case 100 is nearly or completely inverted. The handle slot 413 is seated upon a charging pin 275 (FIG. 13) along the chamber floor 274 that inductively charges the toothbrush 400 when power is delivered to the case 100 preferably through the port 252 as described previously. The handle 412 is axially aligned within the chamber 272 through the engagement of the handle slot 413 with the charging pin 275, and the proximity of the two mating components 413, 275 inductively delivers the charge to the toothbrush handle 412. The chamber walls 273 and the preferably non-circular periphery of the toothbrush handle 412 (see FIGS. 20-21, wherein the periphery has mildly flattened features) are preferably configured to substantially prevent the handle 412 from freely rotating within the chamber 272, and so that the indicator 418 preferably remains oriented toward the front surface 230 of the housing 200 and thereby visible while the handle 412 is seated within the chamber 272 (FIG. 25).

In the illustrated embodiment, the second component 420 of the powered toothbrush 400 (see FIG. 24) is an attachable replacement or refill head configured to be removably coupled to the stem 414 of the first component 410 of the powered toothbrush 400. The second component 420 further comprises a bristle field 422 at the end of a hollow neck portion 424 having indexing slots 426 (FIG. 24) that are sized and configured for engagement with both the indexing tabs 415 on the stem 414 and the indexing tabs or seat 279 along the floor 278 of the second storage chamber 277. The indexing tabs 279 also function to orient the bristle field 422 within the interior 270 so that the bristle field 422 is facing the handle 412 and is oriented adjacent the vent 312 (FIG. 26) so that the bristle field 422 is closest to a location that allows residual moisture on the bristle field 422 to escape from within the interior 270 when the cover 300 is closed.

In a preferred embodiment as shown in FIG. 26, the cover 300 is configured to substantially obfuscate the interior 270 of the case 100 so that the components of the interior 270 are not readily discernible when the cover 300 is closed. The cover 300, however, is also preferably sufficiently light-transmissive to communicate through the cover 300 the presence of an indicator 418 or an indicator light 419 from within the interior 270, so that the user can receive positive confirmation that the toothbrush is being properly charged without having to open the cover 300. In a preferred embodiment with the indicator 418 being oriented outward while the toothbrush handle 412 is stored within the storage location 271, the indicator 418 would preferably be visible or recognizable via illumination 419 through the closed cover 300 (FIG. 26) while the toothbrush is being charged through a power cord 282 connected to the port 252 in the case 100, even though the details of the remaining components of the toothbrush 400 might not be discernible through the cover 300. This enables a user to quickly and discretely confirm that the stored toothbrush is being properly charged.

In an alternative embodiment, an indicator could be provided on the case 100 itself or an aspect of the case 100, rather than on a removable component stored within the case 100, such that the indicator communicates that the case is experiencing a powered or charging condition, which would thereby indicate that the component stored within the case is also experiencing a powering or charging condition. For example, an indicator light may be disposed on the housing 200, such as along a portion of the interior 270 between the first and second storage locations 271, 276. Alternatively, discrete portions of the interior, such as an entire peripheral edge of the housing adjacent the connection between the housing and the cover, may illuminate during a charging or powered condition. Other indicator manifestations and locations are possible. While in the preferred embodiment the cover 300 is substantially translucent, other material properties and compositions are possible. For example, the cover 300 may be substantially opaque or completely opaque, or completely transparent if desired. Furthermore, while it is preferred that the entirety of the cover 300 is substantially translucent for ease of manufacturing for example, it may be more desirable in certain situations if only a portion of the cover 300 is substantially light-transmissive such as, for example, in an area adjacent an illuminated indicator area within the interior 270.

In the illustrated embodiment, the cover 300 is attached to the housing 200 by a hinge 212 defined between the top end 210 of the housing and a location 314 along the cover 300 that is spaced from the top end 310 of the cover 300. The hinge 212 is oriented along an axis 290 (FIG. 4) that is transverse to the longitudinal axis 260 (FIGS. 1 and 4) of the housing 200 with the cover 300 being movable relative to the housing 200 from a closed position (FIGS. 1-8) that occludes the housing interior 270, to a fully-open position (FIGS. 9-16) that exposes the housing interior 270. The hinge 212 also protrudes relative to the rear surfaces 240, 340 of the housing 200 and cover 300, such that when the case 100 is placed in a closed condition on a support surface (not shown) with the rear surfaces 240, 340 adjacent the support surface, the top end 310 of the cover is elevated relative to the bottom end 220 of the housing 200, or in other words the case 100 becomes inclined relative to the support surface by virtue of the case 100 resting on the hinge 212. This incline reinforces the downward positioning of the handle 412 within the chamber 272 and urges the handle 412 into the chamber 272, which helps to maintain the inductive charging contact between the handle slot 413 and chamber pin 275 while the handle 412 is stored within the case 100.

The displaced positioning of the hinge 212 relative to the top end 310 of the cover 300 creates an additional benefit in that when the cover 300 is in a fully-opened condition, the rear surface 340 of the cover 300 adjacent the hinge 212 impacts the upper end of the rear surface 240 of the housing 100 (FIGS. 15-16) and prevents over-rotation of the cover 300 relative to the housing 100.

While various surfaces, locations and orientations of the housing 200, cover 300 and interior 270 have been described to correlate with the illustrated figures, it will be appreciated that the housing, cover and interior can be arranged and configured in a manner other than as shown in the appended drawings, without departing from the scope of the present disclosure.

What is claimed is:

1. A powered toothbrush and case system comprising:
a case having a cover and a housing, the housing comprising a storage chamber;
a power charger located at a bottom of the storage chamber; and
a powered toothbrush having a handle and an indicator on the handle, the powered toothbrush positioned in the storage chamber to be operably coupled to the power charger;
wherein the cover forms a first portion of a front surface of the case and is sufficiently light-transmissive to communicate the presence of the indicator from within the interior, the indicator of the powered toothbrush aligned with and facing the first portion of the front surface of the case; and
wherein the storage chamber is defined by a front chamber wall, a rear chamber wall, a first side chamber wall, and a second side chamber wall, wherein the front chamber wall has a top edge which is at a height below the indicator and the rear chamber wall, first side chamber wall, and second side chamber wall each have a top edge that is at a height above the indicator.

2. The system of claim 1, wherein the top edges of each of the front, rear, first side, and second side chamber walls join adjacent ones of the front, rear, first side, and second side chamber walls tangentially.

3. The system of claim 1, wherein the indicator of the powered toothbrush is visible when the toothbrush is located within the storage chamber.

4. The system of claim 1, wherein the handle of the powered toothbrush further comprises a distal end, the cover of the case completely surrounding the distal end of the powered toothbrush.

5. The system of claim 1, wherein the handle of the powered toothbrush further comprises a longitudinal axis, a plane transverse to the longitudinal axis intersecting the cover of the case and forming a cover cross section that completely surrounds the handle.

6. The system of claim 1, wherein the housing forms a second portion of a front surface of the case.

* * * * *